(12) United States Patent
Szabo et al.

(10) Patent No.: US 7,589,128 B2
(45) Date of Patent: Sep. 15, 2009

(54) PROCESS FOR PREPARATION OF AMORPHOUS FORM OF A DRUG

(75) Inventors: Csaba Szabo, Debrecen (HU); Szabolcs Szoke, Debrecen (HU); Lorant Gyuricza, Nyekljdhiza (HU); Claude Singer, Kfar Saba (IL); Valerie Niddam-Hildesheim, Ein Vered (IL); Greta Sterimbaum, Rishon-Lezion (IL)

(73) Assignee: TEVA Gyógyszergyár Zártkörüen Müködö Részvénytársaság, Debrecen (HU)

( * ) Notice: Subject to any disclaimer, the term of this patent is extended or adjusted under 35 U.S.C. 154(b) by 363 days.

(21) Appl. No.: 11/143,312

(22) Filed: Jun. 1, 2005

(65) Prior Publication Data

US 2005/0272768 A1 Dec. 8, 2005

Related U.S. Application Data

(60) Provisional application No. 60/576,216, filed on Jun. 1, 2004, provisional application No. 60/583,778, filed on Jun. 28, 2004, provisional application No. 60/599,700, filed on Aug. 5, 2004.

(51) Int. Cl.
*A61K 47/00* (2006.01)
(52) U.S. Cl. .................................................. 514/789
(58) Field of Classification Search .................. 514/789
See application file for complete search history.

(56) References Cited

U.S. PATENT DOCUMENTS

| | | | |
|---|---|---|---|
| 3,954,872 A | 5/1976 | Koppe et al. | |
| 3,977,943 A | 8/1976 | Barrow et al. | |
| 4,071,536 A | 1/1978 | Barrow et al. | |
| 4,196,214 A | 4/1980 | Clayton | |
| 4,222,942 A | 9/1980 | O'Hanlon et al. | |
| 4,289,703 A | 9/1981 | Barrow et al. | |
| 4,524,075 A | 6/1985 | Oduro-Yeboah | |
| 4,639,534 A | 1/1987 | Curzons | |
| 4,786,742 A | 11/1988 | Curzons | |
| 4,790,989 A | 12/1988 | Hunter et al. | |
| 4,879,287 A | 11/1989 | Orr et al. | |
| 4,916,155 A | 4/1990 | Baker et al. | |
| 5,191,093 A | 3/1993 | Baker et al. | |
| 5,405,762 A | 4/1995 | Takahashi et al. | |
| 5,436,266 A | 7/1995 | Baker et al. | |
| 5,569,672 A | 10/1996 | Baker et al. | |
| 5,594,026 A | 1/1997 | Greenway et al. | |
| 6,001,870 A | 12/1999 | Henkel | |
| 6,231,875 B1 | 5/2001 | Sun et al. | |
| 6,245,921 B1 | 6/2001 | Barta et al. | |
| 6,306,345 B1 | 10/2001 | Bronshtein et al. | |
| 6,489,358 B2 | 12/2002 | Lavon et al. | |
| 6,506,591 B2 | 1/2003 | Szell et al. | |
| 2002/0004063 A1 | 1/2002 | Zhang | |
| 2002/0028227 A1 | 3/2002 | Yu et al. | |
| 2002/0028843 A1 | 3/2002 | Lavon et al. | |
| 2002/0035061 A1 | 3/2002 | Krieger et al. | |
| 2003/0027292 A1 | 2/2003 | Gulyas et al. | |
| 2003/0100083 A1 | 5/2003 | Szell et al. | |
| 2004/0024052 A1 | 2/2004 | Gyuricza et al. | |
| 2004/0039049 A1 | 2/2004 | Weisman et al. | |
| 2005/0159477 A1 | 7/2005 | Weisman et al. | |
| 2006/0147540 A1 | 7/2006 | Kovacsne-Mezei et al. | |

FOREIGN PATENT DOCUMENTS

| | | |
|---|---|---|
| EP | 0 005 614 | 11/1979 |
| EP | 0 183 424 | 6/1986 |
| EP | 0 251 434 | 1/1988 |
| EP | 1 174 133 | 1/2002 |
| EP | 1 384 721 | 1/2004 |
| GB | 1395907 | 5/1975 |
| GB | 1577730 | 10/1977 |
| GB | 1577545 | 10/1980 |
| JP | 52-70083 | 6/1977 |
| WO | WO 99/27071 | 6/1999 |
| WO | WO 00/40696 | 7/2000 |
| WO | WO 00/46388 | 8/2000 |
| WO | WO 00/46389 | 8/2000 |
| WO | WO 00/71124 A1 | 11/2000 |
| WO | WO 03/006595 | 1/2003 |
| WO | WO 03/063821 A2 | 8/2003 |
| WO | WO 03/063822 A2 | 8/2003 |

OTHER PUBLICATIONS

European Pharmacopoeia, 4th Ed. pp. 1602-1604, Strasbourg, (2001).

Clayton et al. "The Structure and Configuartion of Pseudomonic Acid C" Tetrahedron Letters 1980, vol. 21, pp. 881-884.

O'Hanlon et al. "The Chemistry of Pseudomonic Acid. Part 6. Structure and Preparation of Pseudomonic Acid D" Journal Chemical Society, Perkin Trans. I 1983, pp. 2655-2657.

Feline et al. "Pseudomonic acid. Part 2. Biosynthesis of Pseudomonic Acid A." Journal Chemical Society, Perkin Trans. I. 1977, pp. 309-318.

(Continued)

*Primary Examiner*—Taofiq A Solola
(74) *Attorney, Agent, or Firm*—Kenyon & Kenyon LLP

(57) ABSTRACT

Provided is a process for preparation of amorphous form of an active pharmaceutical ingredient.

33 Claims, 5 Drawing Sheets

OTHER PUBLICATIONS

Mantle et al. "Radiolabelling of the monate moiety in the study of pseudomonic acid biosynthesis." FEMS Microbiol. Lett. 1989, vol. 59, No. 12, pp. 55-58.

Martin et al. "Biosynthetic studies on pseudomonic acid (mupirocin), a novel antibiotic metabolite of *Pseudomonas fluorescens*." Journal Chemical Society, Perkin Trans. I. 1989, pp. 207-209.

Ward et al. "Mupirocin-A review of Its Antibacterial Activity, Pharmacokinetic Properties and Therapeutic Use," Drugs. 1986, vol. 32, No. 5, pp. 425-444.

Hughes et al. "Interaction of pseudomonic acid A with *Escherichia coli* B isoleucyl-tRNA synthetase." Biochemical Journal. 1980, vol. 191, pp. 209-219.

Chain et al. "Pseudomonic Acid. Part 3. Structure of Pseudomonic Acid B" Journal Chemical Society, Perkin Trans. I. 1977, p. 318-322.

Chain et al. "Structure of Pseudomonic Acid, an Antibiotic from *Pseudomonas fluorescens*." Journal of the Chemical Society, Chemical Communications. Jan. 1974, No. 1, pp. 847-848.

Alexander et al. "The Chemistry of Pseudomonic Acid. Part 1. The Absolute Configuration of Pseudomonic Acid A." Journal of the Chemical Society, Perkin Transactions I, Organic and Bio-organic Chemistry. 1978, pp. 561-565.

Palleroni. "Pseudomonaceae." Bergey's Manual of Systematic Bacteriology. 1984, vol. 1, pp. 141-219.

Harry G. Brittain (Ed.) (1999) "Polymorphism in Pharmaceutical Solids" Drugs and the Pharmaceutical Sciences vol. 95, pp. 183-226 Marcel Dekker, Inc. New York, New York.

Demain et al. (Ed.) (1986) Manual of Industrial Microbiology and Biotechnology, American Society of Microbiology, pp. 333-334.

Sikyta et al. (1983) Methods in Industrial Microbiology, John Wiley Sons, pp. 193-199.

Remington: The Science and Practice of Pharmacy, "*Related Granulation Process*" (1995) vol. II, pp. 1627-1628.

A.T. Fuller et al., "Pseudomonic Acid: an Antibiotic Produced by *Pseudomonas fluorescens*," Nature, vol. 234, No. 5329, Dec. 17, 1971, pp. 416-417.

PROCESS FOR PREPARATION OF AMORPHOUS FORM OF A DRUG

CROSS-REFERENCE TO RELATED APPLICATIONS

This application claims the benefits of U.S. Provisional Patent Application Nos. 60/576,216, filed Jun. 1, 2004, 60/583,778, filed Jun. 28, 2004, and 60/599,700, filed Aug. 5, 2004, the contents of all of which are incorporated herein by reference.

FIELD OF THE INVENTION

The present invention provides a process for preparation of amorphous form of a drug, i.e., a pharmaceutical active ingredients (API).

BACKGROUND OF THE INVENTION

Many pharmaceutical solids can exist in different physical forms. Polymorphism is often characterized as the ability of a drug substance to exist as two or more crystalline phases that have different arrangements and/or conformations of the molecules in the crystalline lattice. Amorphous solids consist of disordered arrangements of molecules and do not possess a distinguishable crystal lattice.

Polymorphs of a pharmaceutical solid may have different physical and solid-state chemical (reactivity) properties. These polymorphs differ in internal solid-state structure and, therefore, possess different chemical and physical properties, including packing, thermodynamic, spectroscopic, kinetic, interfacial and mechanical properties. These properties can have a direct impact on drug product quality/performance, including stability, dissolution and bioavailability.

The most stable polymorphic form of a drug substance is often used in a formulation because it has the lowest potential for conversion from one polymorphic form to another. On the other hand, metastable (a form other than the most stable form) and even amorphous forms may be chosen to enhance the bioavailability of the drug product. Amorphous form, being a disorganized solid mass, does not need to lose crystal structure before dissolution in the gastric juices, and thus often has greater bioavailability than a crystalline form.

Even if amorphous form is desirable for formulation, its preparation on industrial scale is often problematic. Many processes used to prepare amorphous form of an active pharmaceutical ingredient are not suitable for industrial scale. In Polymorphism in Pharmaceutical Sciences, Drugs and the Pharmaceutical Sciences, Vol. 95, the authors survey various processes for preparation of amorphous form, and list solidification of melt, reduction of particle size, spray-drying, lyophilization, removal of a solvent from crystalline structure, precipitation of acids and bases by change in pH and others as techniques employed to obtain amorphous form of an active pharmaceutical ingredient.

Many of these processes however are not practical on an industrial scale. For example, to obtain amorphous API by solidification of melt, the API has to be heated beyond its melting point, which may require expenditure of much energy, particularly when the API has a high melting point. Further, the high temperatures may chemically damage the API.

Another one of these processes, lyophilization, for example as shown in EP 1 384 721 and WO03/06595 for amorphous mupirocin calcium, is quite expensive process on large scale, and generally has limited capacity. Further, lyophilization with an organic solvent is often dangerous since it possesses a fire hazard.

Preparation of amorphous form of another active pharmaceutical ingredient, fexofenadine hydrochloride, by spray drying (atomization), is disclosed in WO 00/71124. According to Remington: The Science and Practice of Pharmacy, 19$^{th}$ Ed., vol. II, pg. 1627, spray drying consists of bringing together a highly dispersed liquid and a sufficient volume of hot air to produce evaporation and drying of the liquid droplets. Spray-drying however is often limited to aqueous solutions unless special expensive safety measures are taken. Also in spite of the short contact time, certain undesirable physical and chemical characteristics of the emerging solids are in particular cases unavoidable. The turbulence present in a spray drier as a result of the moving air may alter the product in an undesirable manner. Modifications to the spray drying technique is disclosed in WO 03/063821 and WO 03/063822.

A need exists in the art for a process that allows for preparation of an amorphous form of an active pharmaceutical ingredient on an industrial scale.

SUMMARY OF THE INVENTION

The present invention provides a process for preparing an amorphous form of an active pharmaceutical ingredient comprising: a) providing a chamber having a pressure of less than about 760 mmHg and a temperature of below about 100° C., wherein the chamber has a stirrer and an inlet; b) feeding a solution of the active pharmaceutical ingredient in a solvent having a concentration of more than about 20 m/m %, at a flow rate of about 10 to about 50 cm$^3$/hour/inlet to obtain amorphous form as a sponge or a solid; and c) stirring the sponge or solid with the stirrer to obtain an amorphous powder.

The present invention provides a process for preparing an amorphous form of an active pharmaceutical ingredient comprising: a) providing a chamber having a pressure of less than about 760 mmHg and a temperature of below about 100° C. b) and feeding a solution of the active pharmaceutical ingredient in a solvent having a concentration of more than about 20 m/m %, at a flow rate of about 10 to about 50 cm$^3$/hour/inlet, to obtain amorphous form as a sponge or a solid.

DETAILED DESCRIPTION OF THE INVENTION

Figure 1:
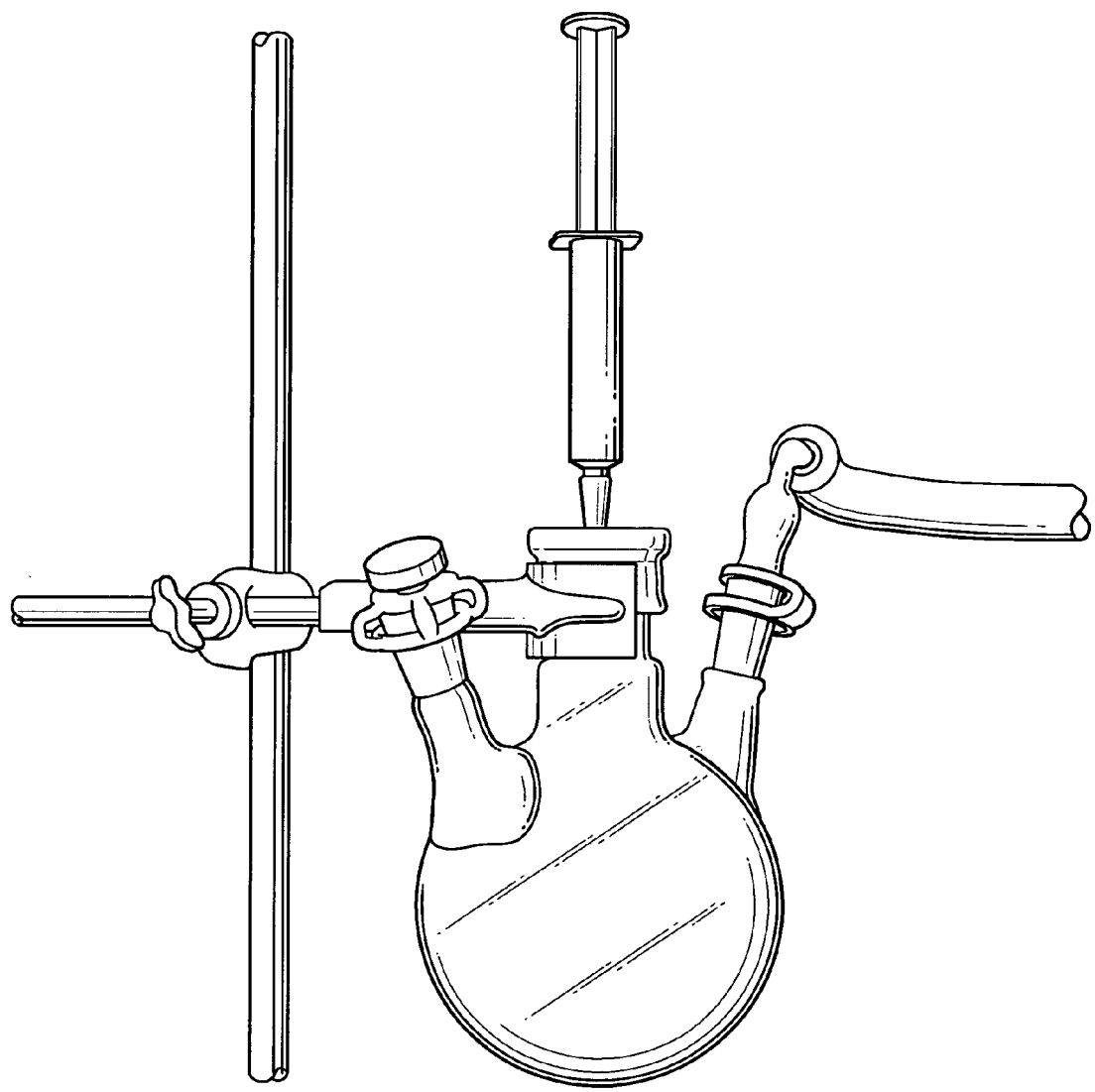
FIG. 1 is an illustration of a laboratory construction for instant drying. In the simplest case, the left intake valve is closed to create a vacuum. Optionally it is possible to use a small inert gas leak.
Figure 2:
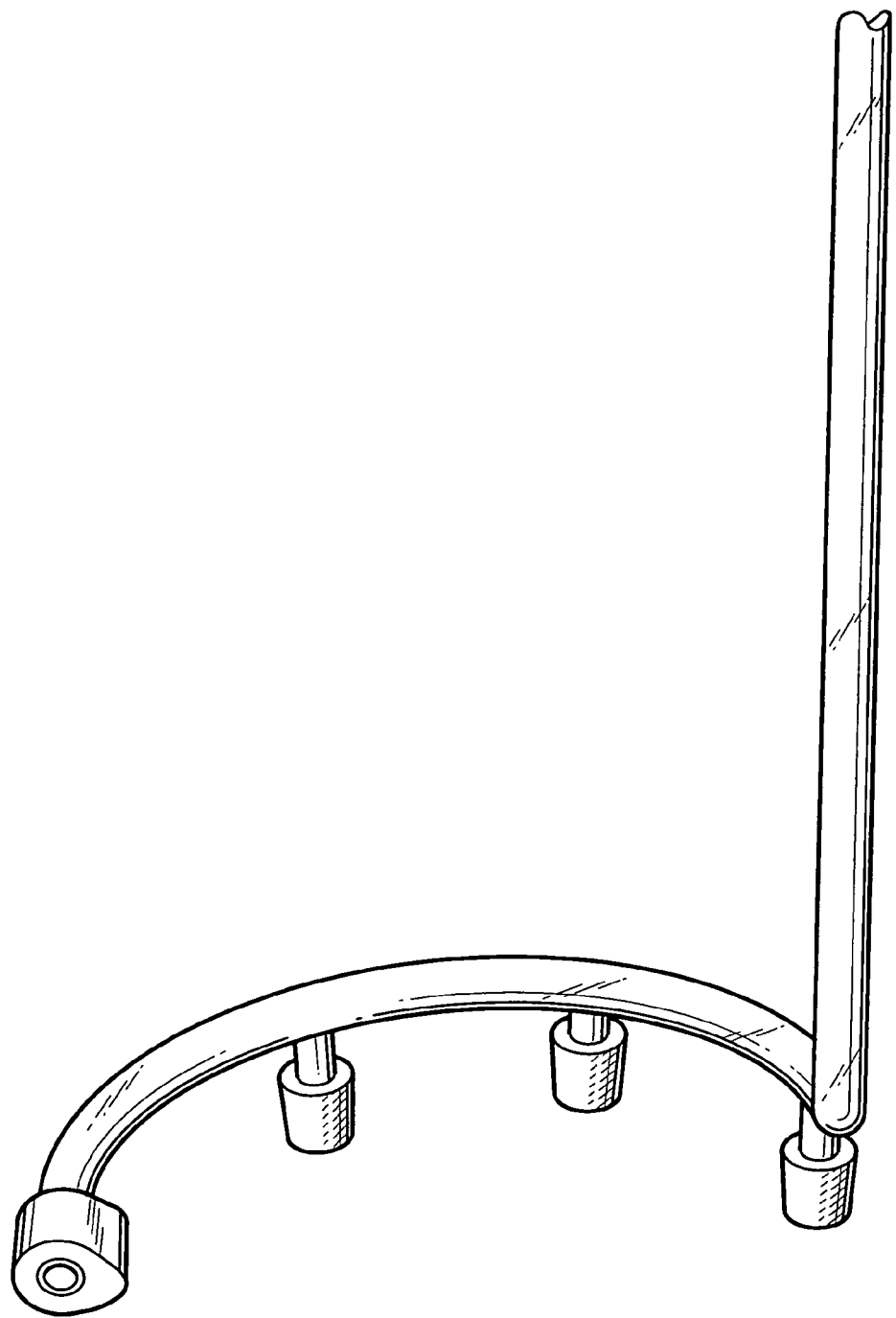
FIG. 2 is an illustration of a distributor in pilot scale.
Figure 3:
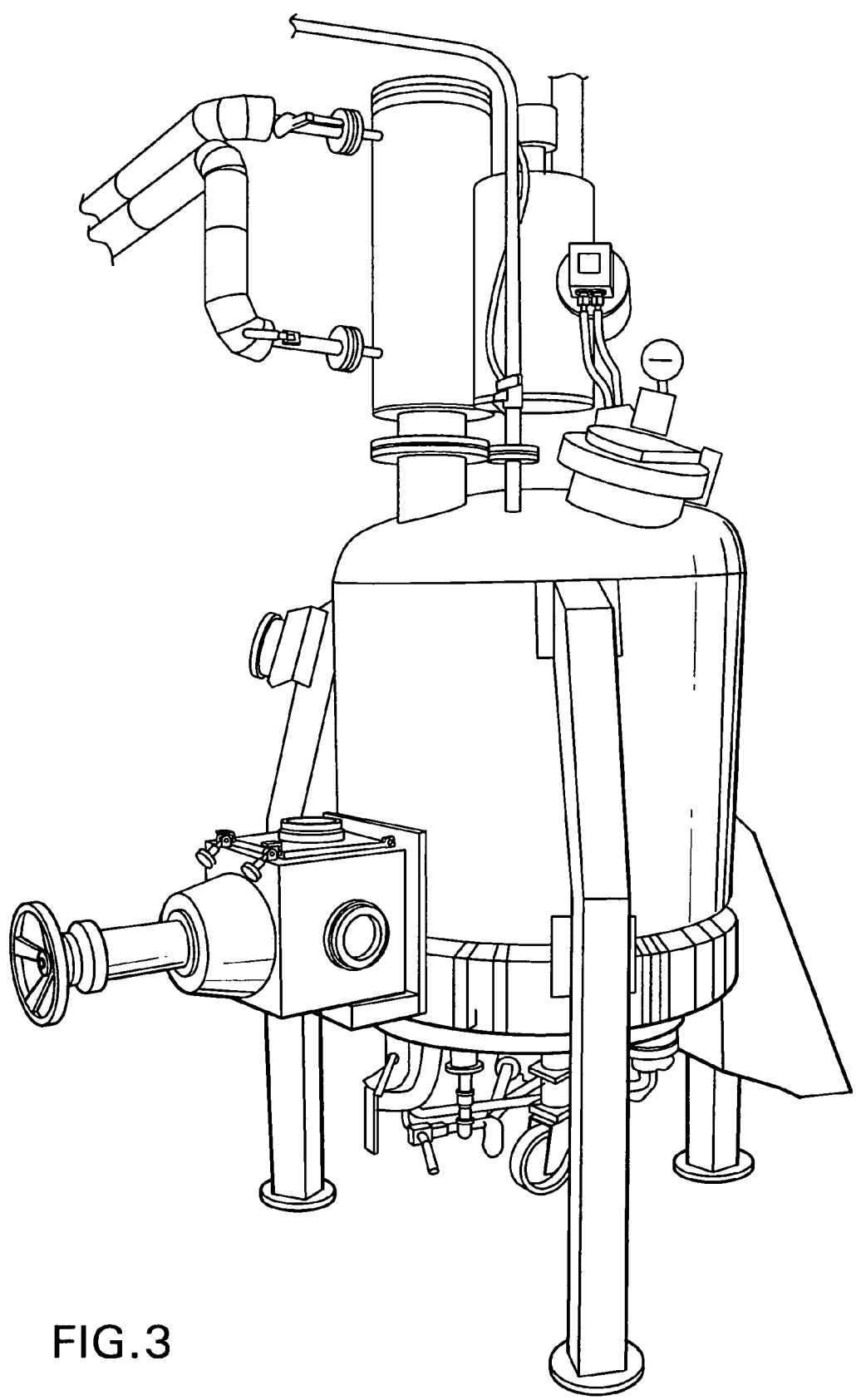
FIG. 3 is an illustration of an industrial dryer.
Figure 4:
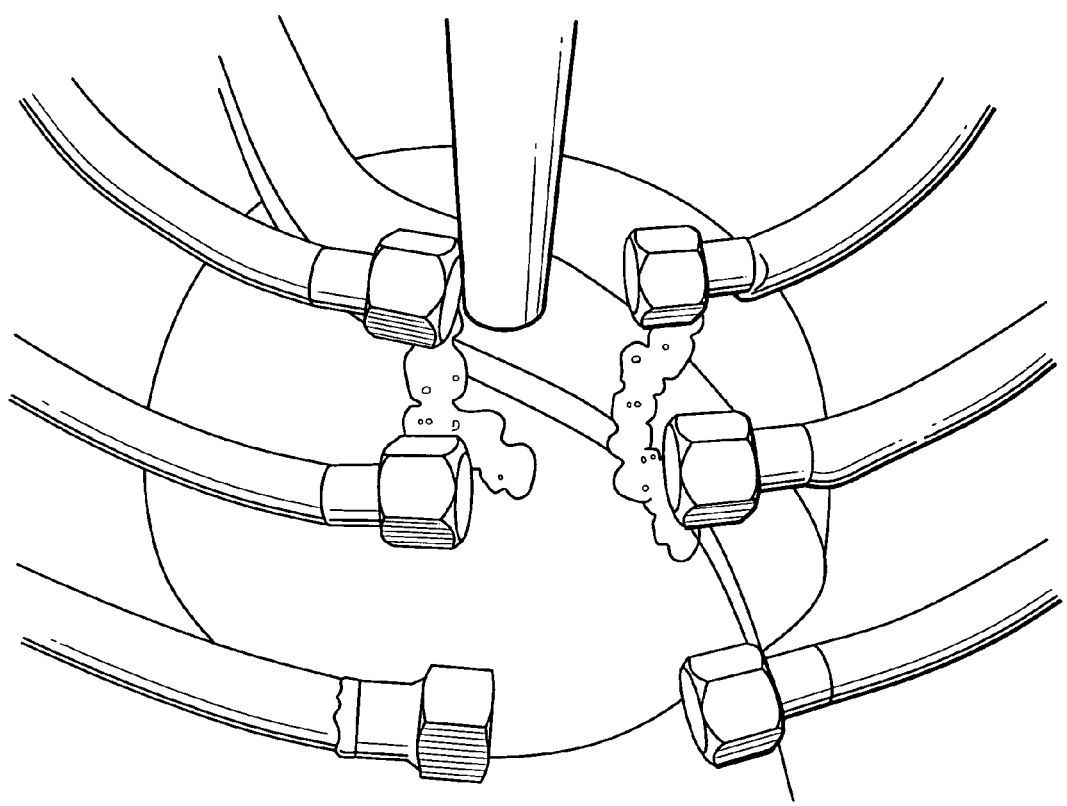
FIG. 4 is an illustration of an industrial feeding system, forming solid API (as sponge).
Figure 5:
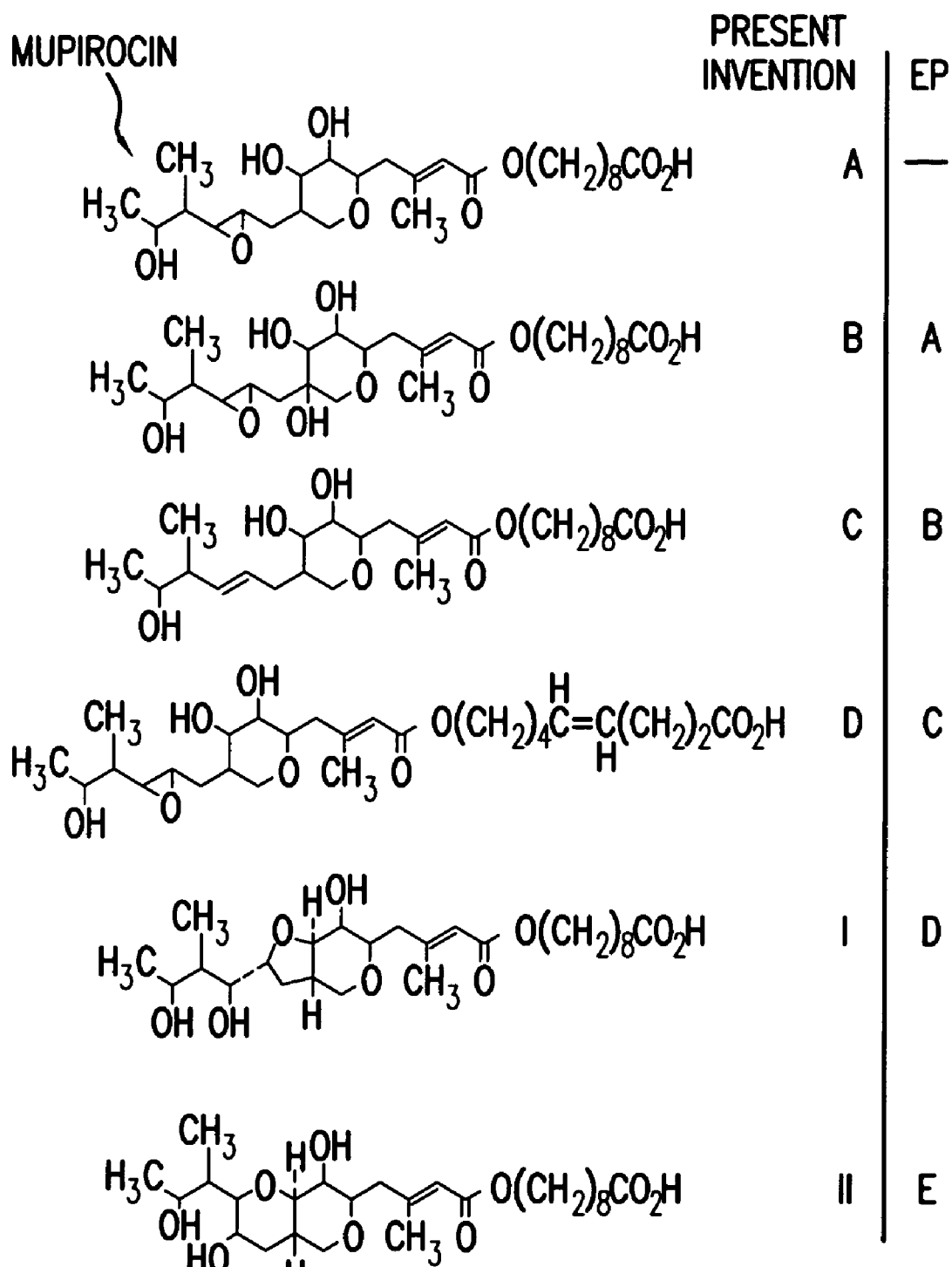
FIG. 5 is an illustration of the various impurities of mupirocin and how they are referred to in the present invention and in the European Pharmacopoeia ("EP").

As used herein, the term "amorphous" refers to a product containing less than 5% crystalline form, preferably less than 3% and more preferably, less than 1%, as measured as area percentage of peaks present in a powder XRD. Presence of amorphous form may be detected by lack of peaks in a powder XRD pattern or lack of a melting point in a DSC thermogram. The area under the peaks in an XRD pattern may be added to obtain total amount of crystalline material. With DSC, presence of endotherms may point to melting of crystalline material.

As used herein, the term "vacuum" refers to a reduced pressure of below about 100 mmHg, more preferably below about 50 mmHg, and most preferably below about 30 mmHg.

As used herein, the term "reduced pressure" refers to a pressure below 760 mmHg or 1 atmosphere.

We have developed a new drying technique-process, which is suitable to produce amorphous form of a drug (including pro-drug), i.e., an active pharmaceutical ingredient. The principle is that amorphous solid is formed when the active pharmaceutical ingredient is dried fast by rapid evaporation from a suitable solvent under reduced pressure. The main driving force of the evaporation in the process of the present invention is a combination of temperature/reduced pressure, and not a hot air flow as in spray drying. The authors of Polymorphism in Pharmaceutical Sciences, Drugs and the Pharmaceutical Sciences, Vol. 95, do not list the process of the present invention as one employed to produce amorphous form.

While other drying techniques may be suitable for laboratory scale, such as less than about 100 grams, the process of the present invention allows for preparing amorphous API on an industrial scale, i.e., a batch of at least about 500 grams, more preferably at least about 1 Kg and most preferably at least about 10 Kg.

The concentration, solvent type, temperature, vacuum, feeding rate are set to such a combination where the API, coming from the inlet, such as a nozzle, precipitates instantly. Otherwise crystalline material can also form. The specific conditions employed are API dependent, however, generally the process may be carried out at a temperature below about 100° C., a reduced pressure and a concentrated solution of the API in a solvent, preferably having a concentration of more than about 20% m/m, and/or concentrated to the point of saturation (solution in equilibrium with a solid solute), and a flow rate of about 10 to about 50 cm$^3$/hour/inlet. These combinations should allow for evaporation of the solvent at the given conditions, i.e., below the vapor pressure of the solvent.

The technique is in principle applicable both for aqueous and organic solvents. However the preferred use is with organic solvents since organic solvents are generally more volatile. Preferred solvents are the easily volatile organic solvents with relatively low boiling point such as $C_1$ to $C_4$ alcohol, $C_3$ to $C_7$ ketone, $C_3$ to $C_7$ ester, $C_5$ to $C_7$ straight or cyclic saturated hydrocarbon or $C_2$ to $C_8$ ethers, or mixtures thereof. Particularly preferred solvents may be selected from methanol, ethanol, acetone, ethylacetate, heptane, hexane, diethylether methyl isobutylether, or mixtures thereof. Especially preferred solvents are methanol or acetone. Preferably technical grade of these solvents are used containing less than about 20% water, more preferably less than about 2% water by volume. The boiling point of the solvent is preferably below about 100° C., more preferably below about 70° C., under atmospheric pressure at room temperature.

The active pharmaceutical ingredient may be in the form of a free base, a free acid, ester or a salt. The solution of the API for drying may be prepared depending on whether the API is a salt or not. For example if the API is an acid, and a salt is desired, the API may be reacted with a base to obtain a solution of the salt (montelukast and NaOH; mupirocin and CaOH). Such reaction may be carried out by suspending or dissolving the API in a solvent, and adding the base. The solution may be filtered if necessary. Examples of salts of API that may be used with the present invention include sodium, calcium, potassium, acetate, benzoate, fumarate, maleate, citrate, tartrate, gentisate, methanesulfonate, ethanesulfonate, benzenesulfonate, laurylsulfonate, taurocholate, hydrochloride and hydrobromide salts. The solution may also be of the API in free acid or free base form, e.g. valsartan.

If the API used has low solubility in a desirable solvent, a polymer may be added to the solution to increase the solubility of the API. A desirable polymer may be chosen based on criteria such as glass transition temperature and effect on bioavailability. Examples of such polymers include those disclosed in WO03/063822. A class of polymers is those derived from cellulose.

The process of the present invention is carried out optimally with a concentrated solution. The last step of the API isolation process is preferably a concentration in a solvent where the API is dissolved. This concentrated solution, with preferably more than about 20 m/m %, more preferably about 20 to about 80 m/m %, more preferably about 60% to about 75%, and/or a solution concentrated to the point of saturation, is fed into a reduced pressure chamber, at a temperature of less than about 100° C., through preferably a sort of nozzles (inlets). The feeding may be carried out by a pump, pressure from another tank, vacuum in the drying chamber or pressure from a syringe device. A chamber may be any reactor, flask, container capable of maintaining the desirable process conditions such as reduced pressure.

In the process of the present invention, the solution is added dropwise or continuously to the drying chamber. One skilled in the art would appreciate that the speed of the addition of the solution will depend on the solvent used, the viscosity of the mixture, and the height of the chamber. The speed may also vary from one API to another. Rate of flow of the solution, if delivered through a nozzle, is preferably in the range of about 10 to about 50 cm$^3$/hour/nozzle (inlet), depending on the concentration, pressure, temperature, properties of the solvent and the API.

The drop of solution explodes (like a popcorn kernel popping) instantaneously in the chamber. This solidification is spontaneous, and does not require further actions such as stirring, and occurs as the solution comes out of the nozzle (inlet) into the drying chamber. This instant evaporation allows for obtaining a phase change (solidification) before the solution contacts the bottom of an industrial sized chamber when fed from the top. A small industrial size chamber has a height of about 0.5 to about 1 meter. It is possible to feed the solution from the side or bottom of the chamber as well.

When the solution reaches the drying chamber, the solvent instantly evaporates, while the dissolved API precipitates as a sponge (a solid foam) or even possibly as a solid with certain API. With mupirocin calcium, the sponge grows due to continuous feeding and hangs on the syringe/nozzles. When the sponge mass reaches a certain mass with mupirocin calcium, it falls down to the bottom of the drying chamber. With other API, it is possible for the solid to fall as it comes out of the nozzle.

Number of inlets for the nozzles in the drying chamber depends on the capacity of vacuum. Vapor removal from the drying chamber can be accelerated by a small leak of an inert gas, preferably nitrogen. Drying equipment preferably contains a stirrer, which is suitable to break the solid, forming a powder.

After breaking the solid, API drying can be continued under reduced pressure, preferably with stirring until the residual solvent concentration reduces to the required FDA level. The solvent level depends on the type of solvent but is preferably no more than about 5000 ppm, more preferably no more than about 4000 ppm, and most preferably no more than about 3000 ppm. The drying of the powder after the stirring is preferably carried out under reduced pressure (below 1 atm), more preferably below about 100 mmHg, most preferably below about 50 mmHg. The temperature is preferably about 30° C. to about 50° C., more preferably about 35° C. to about 45° C. The drying is preferably carried out for about 1 hour to about 10 hour.

The powder can be discharged from the dryer by conventional way, for example via an outlet of a chamber located at the bottom of the chamber, while the stirrer is rotating. A valve may be opened to discharge the powder, and additional force in addition to gravitational force may be used to accelerate the discharge.

The process of the present invention is preferably carried out with a feeding system having a distributor of preferably less than about 3 mm diameter syringe/nozzle, more preferably less than about 2 mm, continuous feeding of API solution, API solution in organic or aqueous solvent, working pressure of preferably less than about 760 mmHg, more preferably less than about 100 mmHg, more preferably less than about 50 mmHg, most preferably less than about 20 mmHg, working temperature of less than about 100° C., preferably about 20° C. to about 80° C., more preferably about 25° C. to about 45° C., optional inert gas flow (such as $N_2$), and a drying chamber with stirrer and a discharge device. While drop-wise addition is possible, scaling up is easier with a syringe and continuous feeding.

The simplest construction of the instant drying in laboratory is a round-bottom flask having a syringe through a septum while vacuum is applied. (FIG. 1.). The instrument of the present invention has a place for injection of the API, which is contemplated to be at top or side of a chamber, but may also be at the bottom of the chamber. The left intake of the instrument shown in FIG. 1 is closed to allow for vacuum generation. The left intake may be used to feed inert gas so as to create a dry environment. In addition to a place for injection, the instrument has an outlet to a vacuum. The instrument may also have a place for applying heat, a discharge place and/or a stirrer.

A sample of the solid from the chamber may be taken with various API and tested for quality assurance. For example, if the process results in more than about 5% crystalline material as area percentage XRD, and less than 5% crystallinity is desired, the process may be changed by manipulating the conditions. If highly pure amorphous API is desired, API having more than about 5% crystallinity may be discarded after the process. Any such API having a crystallinity of 5% or more can be recycled in the process. Batches with less than about 5% crystallinity may be chosen. In some instances crystallinity of less than about 3% or less than about 1% may be desired. Presence of amorphous form may be detected by lack of peaks in a powder XRD pattern or lack of a melting point in a DSC thermogram. The area under the peaks in an XRD pattern may be used in order to calculate the obtained crystallinity.

In addition to mupirocin calcium, montelukast sodium and pimecrolimus as illustrated in the examples, other API for use with this process include fexofenadine hydrochloride, sertraline hydrochloride, moxifloxacin hydrochloride, losartan potassium, esomeprazole magnesium, clopidogrel hydrogensulfate, repaglinide, benazepril hydrochloride, nelfinavir mesylate, donepezil hydrochloride, torasemide, alendronate sodium, fluvastatin sodium, atorvastatin calcium, simvastatin calcium, telmisartan sodium, nelfinavir mesylate, zolenodrate sodium, rosiglitazone maleate, beta-L-2-deoxythymidine and losartan potassium, valganciclovir hydrochloride, repalglinide, levocetririzine dihydrochloride, donepezil hydrochloride, zoledronate sodium, Amorphous rapamycin 42-ester with 3-hydroxy-2-(hydroxymethyl)-2-methylpropionic, duloxetine hydrochloride, BIBN 4096, fluticasone 2-furoate and form of [2-[4-[(4-chlorophenyl)-phenyl methyl]-1-piperazinyl]ethoxy]acetic acid.

Further, U.S. Pat. No. 6,763,607, provides a list of drugs that may be used in the process of the present invention. The list spanning columns 9-11 is incorporated herein by reference.

Pharmaceutical compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with hydrophilic or hydrophobic vehicle. For topical administration the invention provides suitable transdermal delivery systems known in the art, and for nasal delivery there are provided suitable aerosol delivery systems known in the art.

Pharmaceutical compositions of the present invention contain amorphous form of an active pharmaceutical ingredient prepared by the present invention. In addition to the active ingredient(s), the pharmaceutical compositions of the present invention may contain one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate. Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, the active ingredient and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

EXAMPLE 1

Pseudomonic acid (4.0 kg) was dissolved in 10.0 l ethanol at 25-27° C. Potassium hydroxide ethanolic solution (448 grams in 2.6 l ethanol) was added to the pseudomonic acid solution. Calcium chloride ethanolic solution (444 grams in 2.6 l ethanol) was added to the potassium pseudomonate solution. The reaction mixture was stirred at room temperature for an hour. The precipitated potassium chloride was filtered. Part of ethanol was evaporated from the ethanolic calcium pseudomonate solution to reduced volume about 10 l at 40-50° C. The concentration of solution was 24-35 wt %.

Part of ethanol was evaporated from the 90 $cm^3$ of this ethanolic calcium pseudomonate solution obtaining 75 wt % concentration. The concentrated solution was introduced-injected at a feeding rate of 16 g solution/h/nozzle into an evacuated (39-40 mmHg) and heated (jacket temperature 62° C.) 1 l reactor (Chamber) through 2 syringes. After feeding the product was broken by a mechanic stirrer and it was dried under vacuum (39-40 mbar) at 45° C. for 3 hours, then at room temperature for 48 hours. Chemical purity: assay: 95.22%, Mup-II: 0.77%, water content: 0.58%.

EXAMPLE 2

Pseudomonic acid (30 grams) was dissolved in 30 cm$^3$ methanol at 25-27° C. Potassium hydroxide methanolic solution (4.5 grams in 25 cm$^3$ methanol) was added to the pseudomonic acid solution until reaching pH=10.59. The reaction mixture was seeded with potassium chloride crystals. Calcium chloride methanolic solution (4.66 grams in 25 cm$^3$ methanol) was added to the potassium pseudomonate solution until reaching pH=8.58. The reaction mixture was stirred at room temperature for an hour and cooled at 5° C. The precipitated potassium chloride was filtered. Part of methanol was evaporated from the methanolic calcium pseudomonate solution at 40° C. The final concentration of the solution after evaporation was about 75 wt %. The concentrated solution was introduced-injected into an evacuated (1-20 mbar) and heated (jacket temperature 40° C.) 2 liter reactor through 2 syringes. After feeding, the product was broken by a mechanic stirrer and dried under vacuum (13-20 mbar) at 35° C. for 15 hours.

Chemical purity: assay: 94.34%, Mup-II: 0.18%, water content: 0.96%

EXAMPLE 3

Pseudomonic acid (1.4 kgs) was dissolved in 1.4 cm$^3$ methanol at 25-27° C. Potassium hydroxide methanolic solution (180 grams in 1000 cm$^3$ methanol) was added to the pseudomonic acid solution until reaching pH=10.43. The reaction mixture was seeded with potassium chloride crystals. Calcium chloride methanolic solution (186.3 grams in 1000 cm$^3$ methanol) was added to the potassium pseudomonate solution until reaching pH=8.55. The reaction mixture was stirred at room temperature for one hour and cooled at 0° C. The precipitated potassium chloride was filtered. Part of methanol was evaporated from the methanolic calcium pseudomonate solution at 35° C. The final concentration of solution after evaporation was about 60-75 wt %. The concentrated solution was introduced-injected into an evacuated (5-20 mbar) and heated (jacket temperature 40° C.) 30 liter reactor through 8 nozzles. After feeding, the product was broken by a mechanic stirrer and dried under vacuum (5-20 mbar) at 35° C. for 8 hours. The obtained sponge was milled with a grinder. The final product was dried under vacuum (5-20 mbar) for 2 hours at 50° C.

Chemical purity: assay: 97.3%, Mup-II: 0.52%, water content: 1.1%, residual methanol 2440 ppm.

EXAMPLE 4

Pseudomonic acid (13.5 kg) was dissolved in 13.5 l methanol at 25-27° C. Potassium hydroxide methanolic solution (2.2 kg in 12.2 l methanol) was added to the pseudomonic acid solution until reaching pH=10. The reaction mixture seeded with KCl crystals. Calcium chloride methanolic solution (2.2 kg in 12.2 l methanol) was added to the potassium pseudomonate solution until reaching pH=8.56. The reaction mixture stirred at room temperature for an hour. Calcium pseudomonate solution cooled at 0-5° C., and the precipitated KCl filtered. Part of methanol evaporated from the methanolic calcium pseudomonate solution to reduced volume about 18 l at 25° C. jacket temperature. The concentrated solution was introduced-injected into a evacuated (max. 20 mbar) and heated (jacket temperature 35-45° C.) 500 l filter—dryer through 96 nozzles.

In the first step the product dried under vacuum (max. 20 mbar) for 2 hours at 40° C. (jacket temperature). In the second step the product dried under vacuum (max. 20 mbar) for 6 hours at 35° C. (jacket temperature). The obtained sponge powdered with a stirrer and milled with a grinder. The final product was dried under vacuum (max. 20 mbar) for 12 hours at 50-54° C. Chemical purity: assay: 97.8%, Mup-II: 0.59%, water content: 0.6%, residual methanol 2422 ppm.

EXAMPLE 5

Preparation of Montelukast Sodium in Acetone and Instant Drying

Montelukast acid (3 g), NaOH powder (0.24 g, 1.2 eq), and acetone (9 mL) were added to a 100 mL flask equipped with a mechanical stirrer. The reaction was stirred at ambient temperature for 5 hours. The reaction mixture was slowly added dropwise into a 500 mL reactor under vacuum of 1 mm Hg and heated at 35° C. Every drop added was immediately evaporated before reaching the sides or bottom of the reactor. After the end of the addition, the mechanical stirrer was switched on to break the foam formed. The reactor was inverted to collect the powder produced.

EXAMPLE 6

Preparation of Montelukast Sodium in Acetone and Instant Drying

Montelukast sodium salt (1.5 g) and acetone (30 mL) were added to a 100 mL flask equipped with a magnetic stirrer. The solution was stirred at ambient temperature for 1 hour and then filtered under vacuum to remove the insoluble particles. The clear solution was concentrated to half and then transferred to the dropping funnel. The reaction mixture was slowly added dropwise into a 500 mL reactor under vacuum of 1 mm Hg and heated at 45° C. Every drop added immediately evaporated before reaching the sides or bottom of the reactor. After the end of the addition, the mechanical stirrer was switched on to break the foam formed. The reactor was inverted to collect the powder produced.

EXAMPLE 7

Preparation of Montelukast Sodium in MeOH and Instant Drying

Montelukast acid (3 g), NaOH powder (0.24 g, 1.2 eq), and MeOH (15 mL) were added to a 100 mL flask equipped with a mechanical stirrer. The reaction was stirred at ambient temperature for 2 hours until a clear solution was obtained. The reaction mixture was slowly added dropwise into a 500 mL reactor under vacuum of 1 mm Hg and heated at 25° C. Every drop added immediately evaporated before reaching the sides or bottom of the reactor. After the end of the addition, the mechanical stirrer was switched on to break the foam formed. Then the reactor was inverted to collect the powder produced.

The characterization of mupirocin calcium is carried out according to WO03/06595 (US 2004/024052).

EXAMPLE 8

Crude pimecrolimus (2 g) was dissolved in acetone (20 ml). The solution was treated with charcoal (CECA CXV) and evaporated to volume of 1.5 ml (57 m/v %). The solution was injected through a syringe-needle (inner diameter of 0.6 mm) into a flask under vacuum (10-20 mbar) heated by 50° C. water bath. Pimecrolimus solidified instantly and it was collected in the bottom of the flask. Solid foam of pimecrolimus was kept for an additional one hour in the flask under vacuum then pressure was equalized and solid was harvested and crushed. Pimecrolimus (powder) was dried in vacuum oven at 50° C. for overnight. 1.39 g (69.5%) pimecrolimus was obtained. It was analysed by XRD and pure amorphous was obtained. Residual solvent were analysed by GC: acetone 10 ppm.

EXAMPLE 9

Experiment procedure according to the example 8 was followed, but ethylacetate solvent and Norit SX1 activated charcoal was used. Post drying in vacuum oven was done at 60° C. 1.49 g (74.5%) pimecrolimus was obtained. It was analysed by XRD and pure amorphous was obtained. Residual solvent were analysed by GC: ethylacetate 4640 ppm.

Having thus described the invention with reference to particular embodiments and illustrated it with examples, those skilled in the art would appreciate modifications to the invention which do not depart from the spirit and scope of the inventions as disclosed in the specification. All references and publications are incorporated herein by reference.

What is claimed is:

1. A process for preparing an amorphous form of an active pharmaceutical ingredient comprising:
   a) providing a chamber having a pressure of less than about 760 mmHg and a temperature of less than about 100° C., wherein the chamber has a stirrer and an inlet;
   b) feeding a solution of the active pharmaceutical ingredient having a concentration of more than about 20 m/m %, at a flow rate of about 10 to about 50 cm$^3$/hour/inlet to obtain amorphous form as a sponge or a solid; and
   c) stirring the sponge or solid with the stirrer to obtain an amorphous powder.

2. The process of claim 1, wherein the temperature is about 20° C. to about 80° C.

3. The process of claim 1, wherein the temperature is about 25° C. to about 45° C.

4. The process of claim 1, wherein the pressure is less than about 100 mmHg.

5. The process of claim 4, wherein the pressure is less than about 50 mmHg.

6. The process of claim 5, wherein the pressure is less than about 20 mmHg.

7. The process of claim 1, wherein the solution comprises an organic solvent.

8. The process of claim 7, wherein the organic solvent is selected from the group consisting of: $C_1$ to $C_4$ alcohols, $C_3$ to $C_7$ ketones, $C_3$ to $C_7$ esters, $C_5$ to $C_7$ straight, branched or cyclic saturated hydrocarbons, $C_2$ to $C_8$ ethers, and mixtures thereof.

9. The process of claim 8, wherein the alcohol is methanol or ethanol.

10. The process of claim 8, wherein the ketone is acetone.

11. The process of claim 8, wherein the saturated hydrocarbon is heptane or hexane.

12. The process of claim 8, wherein the ester is ethylacetate.

13. The process of claim 8, wherein the ether is diethylether or methyl isobutylether.

14. The process of claim 1, wherein the solution is in an aqueous solvent.

15. The process of claim 7, wherein the organic solvent contains less than about 20% water.

16. The process of claim 1, wherein the solution is saturated.

17. The process of claim 1, wherein the concentration is from about 20 m/m % to about 80 m/m %.

18. The process of claim 17, wherein the solution has a concentration of about 60 m/m % to about 75 m/m %.

19. The process of claim 1, wherein the active pharmaceutical ingredient is in the form of a free base, a free acid, an ester or a salt.

20. The process of claim 19, wherein the salt is selected from the group consisting of mupirocin calcium and montelukast sodium.

21. The process of claim 1, wherein the solution is fed with an inlet that is less than about 3 mm in diameter.

22. The process of claim 21, wherein the solution is fed with an inlet that is less than about 2 mm in diameter.

23. The process of claim 1, wherein the feeding is carried out by a pump, pressure from another tank, vacuum in the drying chamber or pressure from syringe device.

24. The process of claim 1, wherein the solution is fed dropwise.

25. The process of claim 1, wherein the solution is fed in a continuous stream.

26. The process of claim 1, wherein a small leak of an inert gas flows to the chamber.

27. The process of claim 1, wherein the solution is fed at top of the chamber, and solidification takes place before the solution reaches bottom of the chamber.

28. The process of claim 1, wherein the chamber further has an outlet for discharge of the powder.

29. The process of claim 1, further comprising drying the powder under a pressure of less than about 100 mmHg.

30. The process of claim 29, wherein the drying is at a temperature of about 30° C. to about 50° C.

31. The process of claim 1, wherein the process results in less than about 5% crystalline material as area percentage XRD.

32. The process of claim 31, wherein the process results in less than about 3% crystalline material as area percentage XRD.

33. The process of claim 32, wherein the process results in less than about 1% crystalline material as area percentage XRD.

* * * * *

UNITED STATES PATENT AND TRADEMARK OFFICE
CERTIFICATE OF CORRECTION

PATENT NO. : 7,589,128 B2  Page 1 of 1
APPLICATION NO. : 11/143312
DATED : September 15, 2009
INVENTOR(S) : Szabo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 692 days.

Signed and Sealed this

Twenty-first Day of September, 2010

David J. Kappos
*Director of the United States Patent and Trademark Office*